United States Patent [19]

Heidgen

[11] Patent Number: Plant 6,352

[45] Date of Patent: Oct. 25, 1988

[54] GERANIUM PLANT NAMED FIRE CHIEF

[76] Inventor: Charles F. Heidgen, 821 Walnut St., Batavia, Ill. 60510

[21] Appl. No.: 782,733

[22] Filed: Oct. 1, 1985

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new and distinct variety of geranium plant, Fire Chief, characterized by its cascading growth habit; its continuous blooming habit; its small, dark green leaves; its brilliant crimson red, small-sized blossoms; and its heat tolerance.

1 Drawing Sheet

The present discovery, hereinafter referred to by the cultivar name, Fire Chief, relates to a new and distinct geranium plant.

BACKGROUND

Fire Chief is a new and improved variety which has resulted from definite breeding programs and experiments carried on by me in my greenhouses at 821 Walnut St., Batavia, Ill. Our experiments commenced in March, 1977 and are being carried on continuously. This seedling, 79×066E, resulted from a cross between Red Heart, an unpatented, cascade geranium and Berlin, an unpatented, fancy leaf geranium.

Asexual reproduction of Fire Chief has been accomplished from vegetative cuttings in my greenhouses in Batavia, Ill. Examination of plants so propagated has demonstrated that the combination of characteristics herein disclosed for Fire Chief are firmly fixed and retained through successive generations of asexual reproduction.

SUMMARY

The new and patentable characteristics of Fire Chief reside in its cascading growth habit, its continuous blooming habit, its small, dark green leaves, its brilliant red, small-sized blossoms and its heat tolerance.

DESCRIPTION OF DRAWING

The photograph shows the plant and flower of a fully developed geranium of the new variety, Fire Chief.

BOTANIC DESCRIPTION

The Plant

Growth: Fire Chief has a distinctive small, brilliant red, double blossom. It has a compact, procumbent growth habit that gives a cascading effect. The flower head (truss) is of small size and resistant to shattering. Growth rate is rapid, producing a typical 10" flowering basket from four 2¼" plants in 10–12 weeks using standard commercial culture.

Blooming habit: A continuous bloomer throughout the year, outdoors or in the greenhouse. A mature 10" basket would typically produce 14–26 heads at one time. The plant blooms well through summer heat, but may bloom less during the shorter, darker days of winter.

Inflorescence: Small-sized head, rounded, measuring 1¾–2⅔ inches in diameter.

Foliage:

*Quantity.*—Abundant.

*Size.*—Small, 1¾–2¼ inches across.

*Color.*—Ivy Green (0001060/3) with Parsley Green (00962) zone. (The Royal Horticultural Society Horticultural Colour Chart).

*Texture.*—Slightly pubescent upper and lower surface.

Stem: Somewhat slender, short internodes, free branching, procumbent, compact growth habit.

Petiole: Short, 1¾–2 inches long, same color as leaf.

The Flower

Truss:

*Size.*—Small-sized, 1¾–2⅔ inches in diameter.

*Shape.*—Roundish, more flat as it opens.

*Number of florets.*—Variable, range from 14–30, average 20–26.

*Lasting quality.*—Average, blooms last 5–9 days, longer if cool and dry.

Bud:

*Sepals.*—Short, wide, pointed.

*Color.*—Cardinal Red (822) (The Royal Horticultural Society Horticultural Colour Chart).

*Form.*—Round, short, slightly pointed.

Florets:

*Size.*—¾–1 inch across.

*Petalage.*—Double, 9–11 petals.

*Color.*—Turkey Red (721) (The Royal Horticultural Society Horticultural Color Chart).

*Texture.*—Soft and glowing.

*Form.*—Double flowers, petals range from ⅓" to ½" wide.

*Lasting quality.*—Average, floret lasts 3–7 days, truss lasts 5–9 days. In exceptional heat and light, the center of some heads burn.

*Behavior.*—When this plant begins blooming, there are many small, brilliant crimson red blossoms that make stunning show against the small, dark green foliage.

Having thus disclosed my invention, I claim:

1. A new and distinct variety of geranium plant, substantially as shown and described, characterized by its cascading growth habit; its continuous blooming habit; its small dark green leaves; its brilliant crimson red, small-sized blossoms and its heat tolerance.

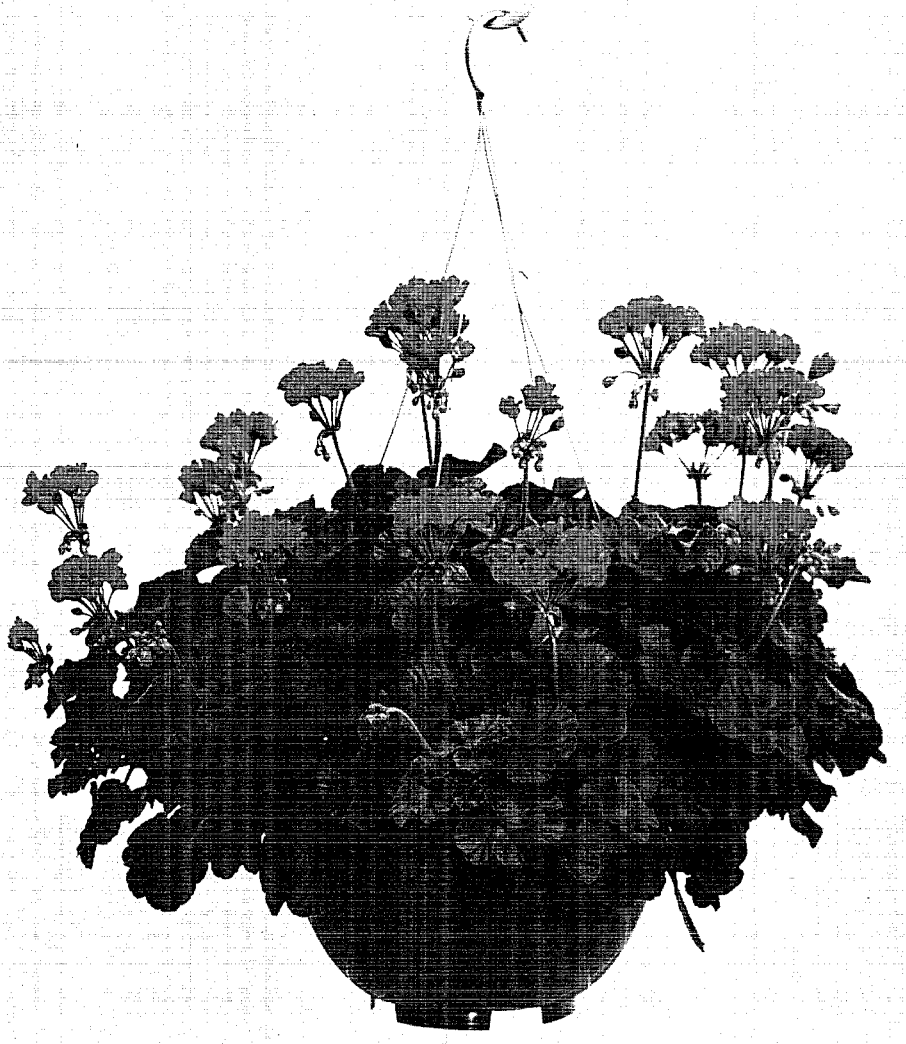

* * * * *